United States Patent [19]  [11] 4,154,703
Umemura et al. [45] May 15, 1979

[54] PROCESS FOR THE PREPARATION OF MALEIC ANHYDRIDE CATALYST

[75] Inventors: Sumio Umemura; Kyoji Ohdan; Fumihiko Sakai; Yasuo Bando; Masataka Fuzinaga, all of Ube, Japan

[73] Assignee: Ube Industries, Inc., Ube, Japan

[21] Appl. No.: 820,338

[22] Filed: Jul. 29, 1977

[30] Foreign Application Priority Data

Oct. 1, 1976 [JP] Japan ................................ 51-117308

[51] Int. Cl.$^2$ .................... B01J 27/14; C07D 307/89
[52] U.S. Cl. ................................ 252/437; 260/346.75
[58] Field of Search ........................................ 252/437

[56] References Cited

U.S. PATENT DOCUMENTS

| B 356,887 | 1/1975 | Schneider | 252/437 X |
|---|---|---|---|
| 3,894,971 | 7/1975 | Reuter | 252/437 |
| 3,907,833 | 9/1975 | Slinkard et al. | 252/437 X |

FOREIGN PATENT DOCUMENTS

| 2505844 | 7/1976 | Fed. Rep. of Germany | 252/437 |
|---|---|---|---|
| 4348736 | 12/1971 | Japan | 252/437 |
| 4889659 | 4/1975 | Japan | 252/437 |

*Primary Examiner*—Delbert E. Gantz
*Assistant Examiner*—William G. Wright
*Attorney, Agent, or Firm*—Miller & Prestia

[57] ABSTRACT

Maleic anhydride is prepared by the catalytic oxidation of unsaturated hydrocarbons having 4 to 6 carbon atoms, at a temperature of from 350° to 500° C., in the presence of a catalyst which is produced by a method wherein a mixture of a titanium oxide and a vanadium compound in an atomic ratio of from 1 to 15 is calcined at a temperature of from 630° to 1000° C. to prepare a precursory catalyst, and wherein a gas mixture containing an organic phosphorus compound and a carrier gas is brought into contact with a mass of the percursory catalyst at a supply rate of the phosphorus compound being from 0.01 to 10 millimoles/hr per 1 ml of the mass of the percursory catalyst and at a temperature of from 350° to 600° C. during when a total amount of from 0.3 to 30 millimoles of the phosphorus compound per 1 ml of the mass of the precursory catalyst passes through the mass of the precursory catalyst.

7 Claims, No Drawings

PROCESS FOR THE PREPARATION OF MALEIC ANHYDRIDE CATALYST

The present invention relates to a process for the preparation of maleic anhydride from unsaturated hydrocarbons having 4 to 6 carbon atoms, a catalyst useful for the process and a method for producing the catalyst.

It is known that maleic anhydride can be produced by the catalytic oxidation of unsaturated hydrocarbons in a gas phase in the presence of a catalyst prepared from a vanadium compound and a titanium oxide. However, such a conventional process is unsatisfactory and not very practical when applied to industry because only a low yield of the maleic anhydride can be obtained therefrom.

On the other hand, it is also known that a catalyst consisting of vanadium, titanium, phosphorus and oxygen is usable for the catalytic oxidation of the unsaturated hydrocarbons to produce the maleic anhydride. However, such a conventional V-Ti-P-O type of catalyst can only be obtained by utilizing a very complicated process. The complexity of this process causes the quality and yield of the resultant maleic anhydride to be uneven. Accordingly, in order to obtain a catalyst which is effective for producing the maleic anhydride with a high yield, the process for producing the catalyst must be strictly controlled.

An object of the present invention is to provide a process for the preparation of maleic anhydride with a high yield, a catalyst useful for the process and having a relatively simple composition, and a method for producing the catalyst in a relatively simple manner.

The above-mentioned object can be attained by using the process, the catalyst and its production method in accordance with the present invention.

The process of the present invention for the preparation of maleic anhydride comprises catalytically oxidizing an unsaturated hydrocarbon having 4 to 6 carbon atoms with molecular oxygen by bringing a feed gas consisting of an unsaturated hydrocarbon-containing gas mixed with a molecular oxygen-containing gas into contact, at a temperature of from 350° to 500° C., with a catalyst of the present invention which contains vanadium, titanium, phosphorus and oxygen and which is produced by employing the method of the present invention comprising mixing a titanium oxide and a vanadium compound in an atomic ratio of Ti to V of from 1 to 15, calcining this mixture at a temperature of from 630° to 1000° C. to form a precursory catalyst, and bringing a gas mixture containing an organic phosphorus compound and a carrier gas, into contact with a mass of the precursory catalyst at a temperature of from 350° to 600° C. and at a supply rate of such phosphorus compound being from 0.01 to 10 millimoles/hr per 1 ml of the mass of the precursory catalyst during when a total amount of from 0.3 to 30 millimoles of the organic phosphorus compound per 1 ml of the mass of the precursory catalyst passes through the mass of the precursory catalyst. In the preparation of the precursory catalyst, a vanadium compound and a titanium oxide is uniformly mixed with each other in an atomic ratio of Ti to V of from 1 to 15. The thus obtained mixture is calcined at a temperature of from 630° to 1000° C. Accordingly, the atomic ratio of Ti to V contained in the resultant precursory catalyst is also in the range of from 1 to 15.

The vanadium compound usable for the preparation of the precursory catalyst may be selected from vanadium oxides, for example, divanadium pentoxide, vanadium dioxide, divanadium trioxide, and vanadium monoxide; vanadium halides, for example, vanadium dichloride, vanadium trichloride and vanadium tetrachloride; and other vanadium compounds, for example, metavanadic acid; ammonium metavanadate, ammonium vanadate and vanadium oxychloride. The more preferable vanadium compounds are divanadium pentoxide and ammonium metavanadate.

The titanium oxide usable for the preparation of the precursory catalyst may have any type crystal structure and, therefore, may be either a rutile type of titanium dioxide or an anatase type of titanium dioxide.

The mixture of the vanadium compound and the titanium oxide can be prepared by using any conventional methods. For example, the mixture may be produced by using a dry mixing method in which a dry powdered vanadium compound is mixed with a dry powdered titanium oxide; by using a semi-dry mixing method in which the dry mixture of the dry powdered vanadium compound and the dry titanium oxide is wetted with a small amount of water, kneaded and then dried; or by using a wet mixing method in which the vanadium compound is dissolved in a solvent, the titanium oxide powder is dispersed in the solution by stirring the mixture, and the resultant dispersion is evaporated into a dry powdered state.

The mixture prepared by any of the above-mentioned mixing methods is calcined at a temperature of from 630° to 1000° C., preferably, from 650° to 900° C. The mixture can be subjected to a molding process before the calcination process or directly calcined in the form of a powder. Since the calcination is carried out at a temperature of 630° C. or more, the entire amount of titanium oxide contained in the resultant precursory catalyst is in the form of a rutile type of titanium dioxide.

If the calcining temperature is lower than 630° C., and the mixture to be calcined contains an anatase type of titanium dioxide, then the titanium dioxide cannot be converted into a rutile type of titanium dioxide. The catalyst produced from the precursor catalyst containing the anatase type of titanium dioxide has a poor catalytic effectiveness and therefore cannot be used to produce a high yield of maleic anhydride.

Although the calcination process is not required to be carried out within a certain period of time, however, it is preferable that the calcination be carried out for a period of 30 minutes or more, more preferably, from 1 to 20 hours.

The precursory catalyst usable for the preparation of the catalyst of the present invention is required to have atomic ratio of Ti to V being 1 to 15, preferably, 3 to 12.

In the case where the atomic ratio of Ti to V is smaller than 1, the yield of the maleic anhydride in the catalytic oxidation of the unsaturated hydrocarbons in the gas phase is undesirably small. An atomic ratio of Ti to V larger than 15 is undesirable because such a large atomic ratio results in an extremely low yield of maleic anhydride obtained by carrying out the above-mentioned catalytic oxidation of the unsaturated hydrocarbons.

In the method for producing the catalyst of the present invention, the precursory catalyst prepared above is treated with a phosphorus compound. Such treatment is preferably effected in a reaction tube. For this purpose, the mass of the precursory catalyst charged into the reaction tube should preferably have a density of from 1.0 to 2.0 g/cm$^3$. The precursory catalyst to be treated may be used in the form as produced by the calcination process, or the catalyst may be pulverized into particles each having a desired size of, for example, from 20 to 200μ. The pulverized precursory catalyst may be molded to form granules each having a desired shape, for example, ball-shaped, right circular cylinder-shaped or square pillar-shaped granules. The shaped granules should preferably each have a volume of from 0.01 to 2 cm$^3$, more preferably, from 0.02 to 1 cm$^3$.

In the conversion of the precursory catalyst to the catalyst of the present invention, a gas mixture containing at least one phosphorus compound and a carrier gas is caused to flow through the reaction tube containing therein the mass of the precursory catalyst heated at a temperature of from 350° to 600° C., preferably, from 400° to 550° C. The gas mixture is supplied into the reaction tube at a supply rate of the phosphorus compound being from 0.01 to 10 millimoles/hr, preferably, from 0.05 to 5 millimoles/hr, per 1 ml of the mass of the precursory catalyst for a period of time during when a total amount of from 0.3 to 30 millimoles, preferably, from 0.5 to 20 millimoles, of the phosphorus compound per 1 ml of the mass of the precursory catalyst passes through the mass of the precursory catalyst.

By the above-mentioned treatment, the surfaces of the precursory catalyst particles are treated with the phosphorus compound for forming the catalyst of the present invention, which catalyst is extremely effective for catalytically oxidizing the unsaturated hydrocarbons in the gas phase to produce a high yield of maleic anhydride.

The phosphorus compound usable for producing the catalyst of the present invention may be selected from trialkyl phosphines, preferably containing alkyl groups each having from 1 to 5 carbon atoms, for example, trimethyl phosphine, triethyl phosphine, and tripropyl phosphine; trialkyl phosphates, preferably containing alkyl groups each having from 1 to 5 carbon atoms, for example, trimethyl phosphate, triethyl phosphate and tripropyl phosphate; and trialkyl phosphite, preferably containing alkyl groups each containing from 1 to 5 carbon atoms, for example, trimethyl phosphite, triethyl phosphite and tripropyl phosphite.

If the supply rate of the organic phosphorus compound is less than 0.01 millimoles/hr per 1 ml of the mass of the precursory catalyst, the surfaces of the precursory catalyst particles cannot be completely uniformly treated with the organic phosphorus compound, or an undesired long period of time is required to complete the treatment of the precursory catalyst with the phosphorus compound.

If the supply rate of the phosphorus compound is greater than 10 millimoles/hr per 1 ml of the mass of the precursory catalyst, the surfaces of the precursory catalyst particles will become excessively treated with the phosphorus compound. Consequently, the resultant catalyst will have a relatively low catalytic effectiveness during the catalytic oxidation of the unsaturated hydrocarbons. Accordingly, when the above-described resultant catalyst is used, a relatively low yield of maleic anhydride is produced.

In the case where the total amount of the phosphorus compound supplied to the reaction tube is smaller than 0.3 millimoles per 1 ml of the mass of the precursory catalyst, the resultant catalyst will be very effective during the catalytic oxidation of the unsaturated hydrocarbons in the gas phase for obtaining a reduced yield of maleic anhydride.

Also, if the total amount of the supplied phosphorus compound is larger than 30 millimoles per 1 ml of the mass of the precursory catalyst, the yield of the maleic anhydride obtained by using the resultant catalyst will be undesirably low.

The treatment of the precursory catalyst with the phosphorus compound is carried out at a temperature ranging from 350° C. to 600° C. If the treating temperature is lower than 350° C. or higher than 600° C., the resultant catalyst will have a relatively low catalytic effectiveness during the catalytic oxidation of the unsaturated hydrocarbons in the gas phase.

The phosphorus compound is mixed with a carrier gas to provide a uniform supply of the phosphorus compound into the reaction tube and to control the rate of treating the precursory catalyst with the phosphorus compound. The carrier gas usable for the above-mentioned purpose can be selected from air, steam, nitrogen gas, or a gas mixture of two or more of the above-mentioned gaseous substances. It is more preferable to use air or a mixture of air and steam as the carrier gas. Also, it is preferable that the gas mixture to be introduced into the reaction tube contains the organic phosphorus compound in a gaseous state in an amount of from 0.01 to 1% by volume.

The resultant catalyst from the above-mentioned method is useful for producing the maleic anhydride. The process for the preparation of the maleic anhydride can be carried out in the following manner.

A feed gas consisting of an unsaturated hydrocarbon-containing gas mixed with a molecular oxygen-containing gas is brought into contact with a mass of the catalyst at a temperature of from 350° to 500° C., preferably, from 370° to 470° C. The mass of the catalyst should preferably have a density of from 1.0 to 2.0 g/cm$^3$ after being charged into a reaction tube. The precursory catalyst may be converted into the resultant catalyst in the same reaction tube.

The unsaturated hydrocarbon-containing gas may be an n-butene-gas, a 1,3-butadiene-gas, a benzene gas, a cyclopentadiene gas, a C$_4$ fraction obtained as a by-product from a cracking process of naphtha, a spent BB fraction obtained by extracting 1,3-butadiene from the C$_4$ fraction, or a gas mixture of butane and n-butene.

The molecular oxygen-containing gas is preferably air. However, the molecular oxygen-containing gas may be a mixture of pure oxygen gas or air with nitrogen or steam.

The catalytic oxidation of the unsaturated hydrocarbons in the gas phase is carried out at a temperature of from 350° to 500° C. in accordance with the process of the present invention. Therefore, if the oxidizing temperature is lower than 350° C., a low reaction (conversion) percentage of the unsaturated hydrocarbons will result. Furthermore, an oxidizing temperature higher than 600° C. will cause a low yield of maleic anhydride.

Except for the oxidation temperature mentioned above, the other oxidation conditions for the unsaturated hydrocarbons are the same as those employed for the conventional catalytic oxidation of organic compounds in the gas phase. For example, the concentration of the unsaturated hydrocarbons to be oxidized in the gas mixture is preferably lower than 2% by volume, more preferably, from 0.1 to 1.8% by volume, in order to prevent the gas mixture from exploding when such a mixture is being supplied to the reaction tube containing the catalyst. Also, it is preferable that the gas mixture be kept in contact with the catalyst for a period of from 0.2 to 3.0 seconds, more preferably, from 0.5 to 2.5 seconds. Furthermore, it is preferable that the molar ratio of the molecular oxygen to the unsaturated hydrocarbon in the gas mixture be in a range of from 10 to 2000, more preferably, from 13 to 200.

In accordance with the method of the present invention, the precursory catalyst, which has a poor catalytic effectiveness during the preparation of the maleic anhydride, can be converted into an extremely effective catalyst for obtaining the maleic anhydride with a high yield, by employing a simple treatment for heating the precursory catalyst with the gas mixture containing the organic phosphorus compound. That is, the method for producing the catalyst of the present invention includes no operational steps which must be carried out under very rigid and difficult conditions, and the process of the present invention can be used to obtain a high yield of maleic anhydride under a stable condition without varying the amount of the yield.

The examples below are presented for the purpose of illustrating the present invention. In the examples, the yield percentage of maleic anhydride and the conversion percentage of the unsaturated hydrocarbons were respectively calculated in accordance with the following equations:

$$\text{Yield percentage of maleic anhydride} = \frac{Y}{X_1} \times 100$$

$$\text{Conversion percentage of an unsaturated hydrocarbon} = \frac{X_1 - X_2}{X_1}$$

wherein $X_1$ denotes an amount by mole of the unsaturated hydrocarbon contained in the feed gas prior to the start of the reaction, $X_2$ denotes an amount by mole of the residual unsaturated hydrocarbon in the feed gas after the completion of the reaction, and Y represents an amount by mole of the resultant maleic anhydride.

EXAMPLES 1 THROUGH 3

In Example 1, a mixture of 7.7 g of ammonium metavanadate with 50 g of an anatase type of titanium dioxide was uniformly kneaded together with a small amount of water and, then, dried at a temperature of 130° C. The dried mixture was molded to form right circular cylinder-shaped pellets each having a diameter of 5 mm and a length of 5 mm. The pellets were calcined at a temperature of 700° C. for 1 hour to provide a precursory catalyst having an atomic ratio of titanium to vanadium of 9.5.

The precursory catalyst pellets in an amount of 48 g were placed in a U-shaped reaction tube made of stainless steel with an inside diameter of 17 mm and a length of 500 mm so that the pellets take up an apparent volume of 30 milliliters. The precursory catalyst in the reaction tube was heated to a temperature of 500° C. A gas mixture containing air and triethyl phosphate was brought into contact with the precursory catalyst in the reaction tube at a flow rate of air being 750 milliliters/minute and at a flow rate of triethyl phosphate being 0.36 milliliters/minute, at a temperature mentioned above for 48 hours. The supply rate of the triethyl phosphate was 0.032 millimoles/hr per 1 milliliter of the precursory catalyst. The total amount of the triethyl phosphate coming into contact with the precursory catalyst during the period of 48 hours was 1.54 millimoles per 1 milliliter of the precursory catalyst.

After completion of the treatment of the precursory catalyst with the triethyl phosphate, the resultant catalyst in the reaction tube was maintained at a temperature of 440° C., and a feed gas containing 0.5% by volume of 1,3-butadiene with the balance being air was brought into contact with the catalyst at such a flow rate that the feed gas remained in the catalyst region for 1.2 seconds. The 1,3-butadiene in the feed gas was catalytically oxidized in the gas phase and converted into maleic anhydride. The resulting conversion percentage of butadiene and the resulting yield percentage of maleic anhydride from the above-mentioned catalytic oxidation are indicated in Table 1 below.

In Example 2, the same procedures as those described in Example 1 were carried out, except that in Example 2 triethyl phosphite was used in place of triethyl phosphate.

In Example 3, procedures identical to those mentioned in Example 1 were carried out, except that in Example 3 triethyl phosphine was employed instead of the triethyl phosphate.

The results of Examples 2 and 3 are also indicated in Table 1 below.

Table 1

| Example No. | Organic phosphorus compound | Conversion of 1,3-butadiene (%) | Yield of maleic anhydride (%) |
|---|---|---|---|
| 1 | Triethyl phosphate | 100 | 64.5 |
| 2 | Triethyl phosphite | 100 | 65.8 |
| 3 | Triethyl phosphine | 100 | 65.5 |

EXAMPLE 4

In order to produce maleic anhydride, the same procedures as those mentioned in Example 1 were carried out except that in Example 4 butene-1 was used in place of 1,3-butadiene and the oxidation temperature was 450° C. instead of 440° C. The conversion of butene-1 was 100% and the yield of maleic anhydride was 57.2%.

EXAMPLES 5 THROUGH 12

In Examples 5 through 10, precursory catalyst pellets were prepared by using the same procedures as those employed in Example 1, except that in Examples 5 through 10, 6.0 g of divanadium pentoxide were used in place of the ammonium metavanadate. The pellets were placed in the same type of reaction tube as the one used in Example 1.

In order to prepare a catalyst, the precursory catalyst placed in the reaction tube was treated with triethyl phosphate by using the same method as that mentioned in Example 1 under the conditions as indicated in Table 2.

In order to produce maleic anhydride by the catalytic oxidation of 1,3-butadiene in the gas phase, the same procedures as those described in Example 1 were carried out by using the above-prepared catalyst. The results of Examples 5 through 10 are indicated in Table 2.

In Example 11, a precursory catalyst was prepared by using the same method as that used in Example 5, except that in Example 11 a rutile type of titanium dioxide was used in place of the anatase type of titanium dioxide and calcination was carried out at a temperature of 650° C. instead of 700° C.

A catalyst was prepared by using the same method as that mentioned in Example 5, except that in Example 11 the above-prepared precursory catalyst was treated with triethyl phosphate under the conditions shown in Table 2.

In order to produce maleic anhydride, 1,3-butadiene was catalytically oxidized in the presence of the above-mentioned catalyst by using the same method as that described in Example 5.

The results of Example 11 are shown in Table 2.

In Example 12, a precursory catalyst was produced by employing the same method as that mentioned in Example 5 except that in Example 12 the atomic ratio of Ti to V in the mixture to be calcined was 6. The precursory catalyst was treated with triethyl phosphate by using the same method as that used in Example 5 under the conditions shown in Table 2. In accordance with the same method as that mentioned in Table 2, 1,3-butadiene was catalytically oxidized in the gas phase to produce maleic anhydride. The results of Example 12 are shown in Table 2.

cursory catalyst was placed in the same reaction tube by following the same method as that used in Example 1. A gas mixture containing triethyl phosphate and air as a carrier gas was introduced into the reaction tube containing the precursory catalyst heated to a temperature of 450° C. The introduction of the gas mixture was carried out at a flow rate of triethyl phosphate being 0.064 millimoles/hr per 1 ml of the precursory catalyst and at a flow rate of air being 2000 ml/hr per 1 ml of the precursory catalyst for 48 hours. The total amount of the triethyl phosphate supplied into the precursory catalyst for 48 hours was 3.02 millimoles per 1 ml of the precursory catalyst.

Thereafter, for producing maleic anhydride, the resultant catalyst was maintained at a temperature of 450° C. in the reaction tube, and a feed gas consisting of 1.0% by volume of a BB fraction and the balance being air was flowed through the reaction tube at such a flow rate that the feed gas was kept in contact with the cata- Table 2

| | | Preparation of precursory catalyst | | | Treatment of precursory catalyst with organic phosphorus compound | | | | Conversion of unsaturated hydrocarbon (%) | Yield of maleic anhydride (%) |
|---|---|---|---|---|---|---|---|---|---|---|
| Example No. | Type of titanium oxide | Type of vanadium compound | Atomic ratio (Ti/V) | Calcination temperature | Supply rate of triethyl phosphate (millimole/hr/ml of precursory catalyst) | Supply rate of air (ml/hr/ml of precursory catalyst) | Temperature (° C.) | Time (hr) | | |
| 5 | Anatase type $TiO_2$ | $V_2O_5$ | 9.5 | 700 | 0.064 | 1500 | 500 | 24 | 100 | 65.5 |
| 6 | " | $V_2O_5$ | 9.5 | 700 | 0.128 | 1500 | 500 | 12 | 100 | 66.3 |
| 7 | " | $V_2O_5$ | 9.5 | 700 | 0.256 | 1500 | 500 | 6 | 100 | 65.8 |
| 8 | " | $V_2O_5$ | 9.5 | 700 | 0.064 | 2000 | 500 | 24 | 100 | 65.9 |
| 9 | " | $V_2O_5$ | 9.5 | 700 | 0.064 | 1500 | 450 | 24 | 100 | 66.0 |
| 10 | " | $V_2O_5$ | 9.5 | 700 | 0.042 | 1500 | 470 | 30 | 100 | 64.2 |
| 11 | Rutile type $TiO_2$ | $V_2O_5$ | 9.5 | 650 | 0.064 | 1500 | 500 | 24 | 100 | 66.7 |
| 12 | Anatase type $TiO_2$ | $V_2O_5$ | 6 | 700 | 0.064 | 1500 | 440 | 24 | 100 | 64.8 |

EXAMPLES 13 THROUGH 15

In each of the Examples 13 through 15, a catalyst was produced by using the same method as that used in Example 5 except that in these Examples the precursory catalyst was prepared at the respective calcining temperature shown in Table 3.

In each of the Examples 13 through 15, maleic anhydride was prepared from 1,3-butadiene by using the same method as that used in Example 5 except that in Examples 13 through 15 the above-described catalyst was used under the conditions indicated in Table 3.

The results of Examples 13 through 15 are shown in Table 3.

lyst for 1.5 seconds. The BB fraction had the following composition.

| Component | Content (% by weight) |
|---|---|
| Butene -1 | 11.15 |
| Butene -2 | 8.63 |
| Isobutene | 27.37 |
| 1,3-Butadiene | 47.00 |
| Butane | 4.77 |
| Other hydrocarbons | 1.08 |

As a result of the above-mentioned reaction, the conversion of the BB fraction was 93.2%, and the yield of Table 3

| | | Catalytic oxidation of 1,3-butadiene | | | | |
|---|---|---|---|---|---|---|
| Example No. | Calcining temperature (° C.) | Concentration of 1,3-butadiene in feed gas (% by volume) | Contact time (sec) | Temperature (° C.) | Conversion of 1,3-butadiene (%) | Yield of maleic anhydride (%) |
| 13 | 650 | 0.4 | 1.2 | 440 | 100 | 67.5 |
| 14 | 700 | 1.0 | 1.2 | 450 | 100 | 63.8 |
| 15 | 700 | 1.0 | 1.8 | 470 | 100 | 65.3 |

EXAMPLE 16

A precursory catalyst was prepared by using the same method as that employed in Example 1. The premaleic anhydride from butene-1, butene-2 and 1,3-butadiene in the BB fraction was 62.0% by mole.

COMPARISON EXAMPLE 1

The same procedures as those described in Example 1 were carried out except that the precursory catalyst was used as a catalyst for the catalytic oxidation of 1,3-butadiene without the treatment of the precursory catalyst with triethyl phosphate. The conversion of 1,3-butadiene was 100%, and a very poor yield of maleic anhydride, i.e., 27.3% by mole, was obtained.

COMPARISON EXAMPLE 2

The same procedures as those described in Example 1 were carried out, except that the precursory catalyst in Comparison Example 2 was prepared at a temperature of 600° C.

The conversion of 1,3-butadiene was 100%, and maleic anhydride was obtained in a very poor yield of 10% by mole.

What is claimed is:

1. A method for producing a catalyst usable for the preparation of maleic anhydride by catalytic oxidation of unsaturated hydrocarbon having 4 to 6 carbon atoms, comprising mixing a titanium oxide and a vanadium compound, in an atomic ratio of Ti to V of from 1 to 15, said vanadium compound being selected from the group consisting of vanadium oxides, vanadium halides, metavanadic acid, ammonium vanadate and vanadium oxychlorides, calcining said mixture at a temperature of from 630° to 1000° C. to form a precursory catalyst, and bringing a gas mixture containing an organic phosphorus compound selected from the group consisting of phosphines, trialkyl phosphates and trialkyl phosphites, and a carrier gas into contact with a mass of said precursory catalyst at a temperature of from 350° to 600° C. and at a supply rate of said phosphorus compound of from 0.01 to 10 millimoles/hr. per 1 ml. of the mass of said precursory catalyst during when a total amount of from 0.3 to 30 millimoles, of said organic phosphorus compound per 1 ml. of the mass of said precursory catalyst passes through the mass of said precursory catalyst.

2. A method as claimed in claim 1, wherein said precursory catalyst is granulated into granules each having a volume of from 0.01 to 2 $cm^3$.

3. A method as claimed in claim 1, wherein said titanium oxide is either a rutile type or an anatase type of titanium dioxides.

4. A method as claimed in claim 1, wherein said carrier gas is selected from air, steam, nitrogen and mixtures of two or more of the above-mentioned gases.

5. A method as claimed in claim 1, wherein said organic phosphorus compound is contained in an amount of from 0.01 to 1% by gas volume in said gas mixture.

6. A method as claimed in claim 1, wherein said vanadium compound is either a vanadium oxide or an ammonium metavanadate.

7. A method as claimed in claim 1, wherein each of the alkyl groups in said organic phosphorus compound has 1 to 5 carbon atoms.

* * * * *

UNITED STATES PATENT AND TRADEMARK OFFICE
CERTIFICATE OF CORRECTION

PATENT NO. : 4,154,703
DATED : May 15, 1979
INVENTOR(S) : Sumio Umemura et al

It is certified that error appears in the above-identified patent and that said Letters Patent are hereby corrected as shown below:

Title page, Item #73, delete "Ube Industries, Inc." and substitute therefor --Ube Industries, Ltd.--.

Signed and Sealed this

Twenty-fifth Day of September 1979

[SEAL]

Attest:

Attesting Officer

LUTRELLE F. PARKER
*Acting Commissioner of Patents and Trademarks*